(12) United States Patent
Landes et al.

(10) Patent No.: US 11,541,092 B2
(45) Date of Patent: Jan. 3, 2023

(54) COMPOSITION FOR INCREASING SEXUAL DESIRE OR PLEASURE

(71) Applicant: Libby & Co LLC, Corona Del Mar, CA (US)

(72) Inventors: Bernard M. Landes, Laguna Niguel, CA (US); Elizabeth J. Shirley, Austin, TX (US); Ryan Shea, Eagle, ID (US); Brett M. Hales, Newport Beach, CA (US)

(73) Assignee: Libby and Co. LLC, Corona Del Mar, CA (US)

( * ) Notice: Subject to any disclaimer, the term of this patent is extended or adjusted under 35 U.S.C. 154(b) by 0 days.

(21) Appl. No.: 17/224,094

(22) Filed: Apr. 6, 2021

(65) Prior Publication Data

US 2021/0315954 A1  Oct. 14, 2021

Related U.S. Application Data

(60) Provisional application No. 63/006,965, filed on Apr. 8, 2020.

(51) Int. Cl.

| | |
|---|---|
| *A61K 36/258* | (2006.01) |
| *A61K 31/522* | (2006.01) |
| *A61K 31/714* | (2006.01) |
| *A61K 9/00* | (2006.01) |
| *A61K 36/88* | (2006.01) |
| *A61K 31/375* | (2006.01) |
| *A61K 31/4164* | (2006.01) |
| *A61K 33/00* | (2006.01) |

(52) U.S. Cl.
CPC .......... *A61K 36/258* (2013.01); *A61K 9/0053* (2013.01); *A61K 31/375* (2013.01); *A61K 31/4164* (2013.01); *A61K 31/522* (2013.01); *A61K 31/714* (2013.01); *A61K 33/00* (2013.01); *A61K 36/88* (2013.01)

(58) Field of Classification Search
None
See application file for complete search history.

(56) References Cited

U.S. PATENT DOCUMENTS

| | | | | |
|---|---|---|---|---|
| 2002/0192307 | A1* | 12/2002 | Wuh | A61K 36/185 514/565 |
| 2008/0057162 | A1* | 3/2008 | Brucker | A23F 5/14 426/309 |
| 2012/0141611 | A1* | 6/2012 | Landes | A61K 31/728 424/769 |

OTHER PUBLICATIONS

Anaya, A. et al. Metabolism and Ecology of Purine Alkaloids. Frontiers in Bioscience 11:2354-2370, Sep. 2006. (Year: 2006).*

* cited by examiner

*Primary Examiner* — Ralph J Gitomer
(74) *Attorney, Agent, or Firm* — Steve Hassid; Partners Law Group Inc.

(57) ABSTRACT

Methods and compositions for increasing sexual desire and pleasure in a mammal are provided. In at least one embodiment, a composition comprising at least (1) damiana (*Turnera diffusa*) extract, (2) theacrine, (3) *ginseng*, (4) vitamin C, (5) vitamin B12, (6) saffron, (7) potassium nitrate is provided as an oral dosage unit. The claimed composition provides improved sexual desire and pleasure in female mammals.

13 Claims, 13 Drawing Sheets

Female Sexual Function Index (FSFI) ©

Subject Identifier _____     Date _____

INSTRUCTIONS: These questions ask about your sexual feelings and responses during the past 4 weeks. Please answer the following questions as honestly and clearly as possible. Your responses will be kept completely confidential. In answering these questions the following definitions apply:

<u>Sexual activity</u> can include caressing, foreplay, masturbation and vaginal intercourse.

<u>Sexual intercourse</u> is defined as penile penetration (entry) of the vagina.

<u>Sexual stimulation</u> includes situations like foreplay with a partner, self-stimulation (masturbation), or sexual fantasy.

CHECK <u>ONLY</u> ONE BOX PER QUESTION.

<u>Sexual desire</u> or <u>interest</u> is a feeling that includes wanting to have a sexual experience, feeling receptive to a partner's sexual initiation, and thinking or fantasizing about having sex.

1. Over the past 4 weeks, how often did you feel sexual desire or interest?

☐ Almost always or always
    ☐ Most times (more than half the time)
    ☐ Sometimes (about half the time)
    ☐ A few times (less than half the time)
    ☐ Almost never or never 2. Over the past 4 weeks, how would you rate your level (degree) of sexual desire or interest?

☐ Very high
    ☐ High
    ☐ Moderate
    ☐ Low
    ☐ Very low or none at all

FIG. 1

Sexual arousal is a feeling that includes both physical and mental aspects of sexual excitement. It may include feelings of warmth or tingling in the genitals, lubrication (wetness), or muscle contractions.

3. Over the past 4 weeks, how often did you feel sexually aroused ("turned on") during sexual activity or intercourse?

- ☐ No sexual activity
- ☐ Almost always or always
- ☐ Most times (more than half the time)
- ☐ Sometimes (about half the time)
- ☐ A few times (less than half the time)
- ☐ Almost never or never 4. Over the past 4 weeks, how would you rate your level of sexual arousal ("turn on") during sexual activity or intercourse?

- ☐ No sexual activity
- ☐ Very high
- ☐ High
- ☐ Moderate
- ☐ Low
- ☐ Very low or none at all 5. Over the past 4 weeks, how confident were you about becoming sexually aroused during sexual activity or intercourse?

- ☐ No sexual activity
- ☐ Very high confidence
- ☐ High confidence
- ☐ Moderate confidence
- ☐ Low confidence
- ☐ Very low or no confidence 6. Over the past 4 weeks, how often have you been satisfied with your arousal (excitement) during sexual activity or intercourse?

- ☐ No sexual activity
- ☐ Almost always or always
- ☐ Most times (more than half the time)
- ☐ Sometimes (about half the time)
- ☐ A few times (less than half the time)
- ☐ Almost never or never

FIG. 2

7. Over the past 4 weeks, how often did you become lubricated ("wet") during sexual activity or intercourse?

☐ No sexual activity
    ☐ Almost always or always
    ☐ Most times (more than half the time)
    ☐ Sometimes (about half the time)
    ☐ A few times (less than half the time)
    ☐ Almost never or never 8. Over the past 4 weeks, how difficult was it to become lubricated ("wet") during sexual activity or intercourse?

☐ No sexual activity
    ☐ Extremely difficult or impossible
    ☐ Very difficult
    ☐ Difficult
    ☐ Slightly difficult
    ☐ Not difficult 9. Over the past 4 weeks, how often did you maintain your lubrication ("wetness") until completion of sexual activity or intercourse?

☐ No sexual activity
    ☐ Almost always or always
    ☐ Most times (more than half the time)
    ☐ Sometimes (about half the time)
    ☐ A few times (less than half the time)
    ☐ Almost never or never 10. Over the past 4 weeks, how difficult was it to maintain your lubrication ("wetness") until completion of sexual activity or intercourse?

☐ No sexual activity
    ☐ Extremely difficult or impossible
    ☐ Very difficult
    ☐ Difficult
    ☐ Slightly difficult
    ☐ Not difficult

FIG. 3

11. Over the past 4 weeks, when you had sexual stimulation or intercourse, how often did you reach orgasm (climax)?

☐ No sexual activity
    ☐ Almost always or always
    ☐ Most times (more than half the time)
    ☐ Sometimes (about half the time)
    ☐ A few times (less than half the time)
    ☐ Almost never or never 12. Over the past 4 weeks, when you had sexual stimulation or intercourse, how difficult was it for you to reach orgasm (climax)?

☐ No sexual activity
    ☐ Extremely difficult or impossible
    ☐ Very difficult
    ☐ Difficult
    ☐ Slightly difficult
    ☐ Not difficult 13. Over the past 4 weeks, how satisfied were you with your ability to reach orgasm (climax) during sexual activity or intercourse?

☐ No sexual activity
    ☐ Very satisfied
    ☐ Moderately satisfied
    ☐ About equally satisfied and dissatisfied
    ☐ Moderately dissatisfied
    ☐ Very dissatisfied 14. Over the past 4 weeks, how satisfied have you been with the amount of emotional closeness during sexual activity between you and your partner?

☐ No sexual activity
    ☐ Very satisfied
    ☐ Moderately satisfied
    ☐ About equally satisfied and dissatisfied
    ☐ Moderately dissatisfied
    ☐ Very dissatisfied

FIG. 4

15. Over the past 4 weeks, how satisfied have you been with your sexual relationship with your partner?

- ☐ Very satisfied
- ☐ Moderately satisfied
- ☐ About equally satisfied and dissatisfied
- ☐ Moderately dissatisfied
- ☐ Very dissatisfied 16. Over the past 4 weeks, how satisfied have you been with your overall sexual life?

- ☐ Very satisfied
- ☐ Moderately satisfied
- ☐ About equally satisfied and dissatisfied
- ☐ Moderately dissatisfied
- ☐ Very dissatisfied 17. Over the past 4 weeks, how often did you experience discomfort or pain <u>during</u> vaginal penetration?

- ☐ Did not attempt intercourse
- ☐ Almost always or always
- ☐ Most times (more than half the time)
- ☐ Sometimes (about half the time)
- ☐ A few times (less than half the time)
- ☐ Almost never or never 18. Over the past 4 weeks, how often did you experience discomfort or pain <u>following</u> vaginal penetration?

- ☐ Did not attempt intercourse
- ☐ Almost always or always
- ☐ Most times (more than half the time)
- ☐ Sometimes (about half the time)
- ☐ A few times (less than half the time)
- ☐ Almost never or never 19. Over the past 4 weeks, how would you rate your level (degree) of discomfort or pain during or following vaginal penetration?

- ☐ Did not attempt intercourse
- ☐ Very high
- ☐ High
- ☐ Moderate
- ☐ Low
- ☐ Very low or none at all

*Thank you for completing this questionnaire*

FIG. 5

FSFI SCORING APPENDIX

| Question | Response Options |
|---|---|
| 1. Over the past 4 weeks, how often did you feel sexual desire or interest? | 5 = Almost always or always<br>4 = Most times (more than half the time)<br>3 = Sometimes (about half the time)<br>2 = A few times (less than half the time)<br>1 = Almost never or never |
| 2. Over the past 4 weeks, how would you rate your level (degree) of sexual desire or interest? | 5 = Very high<br>4 = High<br>3 = Moderate<br>2 = Low<br>1 = Very low or none at all |
| 3. Over the past 4 weeks, how often did you feel sexually aroused ("turned on") during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |
| 4. Over the past 4 weeks, how would you rate your level of sexual arousal ("turn on") during sexual activity or intercourse? | 0 = No sexual activity<br>5 = Very high<br>4 = High<br>3 = Moderate<br>2 = Low<br>1 = Very low or none at all |
| 5. Over the past 4 weeks, how confident were you about becoming sexually aroused during sexual activity or intercourse? | 0 = No sexual activity<br>5 = Very high confidence<br>4 = High confidence<br>3 = Moderate confidence<br>2 = Low confidence<br>1 = Very low or no confidence |
| 6. Over the past 4 weeks, how often have you been satisfied with your arousal (excitement) during sexual activity or intercourse? | 0 = No sexual activity<br>5 = Almost always or always<br>4 = Most times (more than half the time)<br>3 = Sometimes (about half the time)<br>2 = A few times (less than half the time)<br>1 = Almost never or never |

FIG. 6

7. Over the past 4 weeks, how often did you become lubricated ("wet") during sexual activity or intercourse?

0 = No sexual activity
5 = Almost always or always
4 = Most times (more than half the time)
3 = Sometimes (about half the time)
2 = A few times (less than half the time)
1 = Almost never or never 8. Over the past 4 weeks, how difficult was it to become lubricated ("wet") during sexual activity or intercourse?

0 = No sexual activity
1 = Extremely difficult or impossible
2 = Very difficult
3 = Difficult
4 = Slightly difficult
5 = Not difficult 9. Over the past 4 weeks, how often did you maintain your lubrication ("wetness") until completion of sexual activity or intercourse?

0 = No sexual activity
5 = Almost always or always
4 = Most times (more than half the time)
3 = Sometimes (about half the time)
2 = A few times (less than half the time)
1 = Almost never or never 10. Over the past 4 weeks, how difficult was it to maintain your lubrication ("wetness") until completion of sexual activity or intercourse?

0 = No sexual activity
1 = Extremely difficult or impossible
2 = Very difficult
3 = Difficult
4 = Slightly difficult
5 = Not difficult 11. Over the past 4 weeks, when you had sexual stimulation or intercourse, how often did you reach orgasm (climax)?

0 = No sexual activity
5 = Almost always or always
4 = Most times (more than half the time)
3 = Sometimes (about half the time)
2 = A few times (less than half the time)
1 = Almost never or never 12. Over the past 4 weeks, when you had sexual stimulation or intercourse, how difficult was it for you to reach orgasm (climax)?

0 = No sexual activity
1 = Extremely difficult or impossible
2 = Very difficult
3 = Difficult
4 = Slightly difficult
5 = Not difficult

FIG. 7

13. Over the past 4 weeks, how satisfied were you with your ability to reach orgasm (climax) during sexual activity or intercourse?

0 = No sexual activity
5 = Very satisfied
4 = Moderately satisfied
3 = About equally satisfied and dissatisfied
2 = Moderately dissatisfied
1 = Very dissatisfied 14. Over the past 4 weeks, how satisfied have you been with the amount of emotional closeness during sexual activity between you and your partner?

0 = No sexual activity
5 = Very satisfied
4 = Moderately satisfied
3 = About equally satisfied and dissatisfied
2 = Moderately dissatisfied
1 = Very dissatisfied 15. Over the past 4 weeks, how satisfied have you been with your sexual relationship with your partner?

5 = Very satisfied
4 = Moderately satisfied
3 = About equally satisfied and dissatisfied
2 = Moderately dissatisfied
1 = Very dissatisfied 16. Over the past 4 weeks, how satisfied have you been with your overall sexual life?

5 = Very satisfied
4 = Moderately satisfied
3 = About equally satisfied and dissatisfied
2 = Moderately dissatisfied
1 = Very dissatisfied 17. Over the past 4 weeks, how often did you experience discomfort or pain during vaginal penetration?

0 = Did not attempt intercourse
1 = Almost always or always
2 = Most times (more than half the time)
3 = Sometimes (about half the time)
4 = A few times (less than half the time)
5 = Almost never or never 18. Over the past 4 weeks, how often did you experience discomfort or pain following vaginal penetration?

0 = Did not attempt intercourse
1 = Almost always or always
2 = Most times (more than half the time)
3 = Sometimes (about half the time)
4 = A few times (less than half the time)
5 = Almost never or never 19. Over the past 4 weeks, how would you rate your level (degree) of discomfort or pain during or following vaginal penetration?

0 = Did not attempt intercourse
1 = Very high
2 = High
3 = Moderate
4 = Low
5 = Very low or none at all

FIG. 8

| Domain | Questions | Score Range | Factor | Minimum Score | Maximum Score | Score |
|---|---|---|---|---|---|---|
| Desire | 1, 2 | 1 – 5 | 0.6 | 1.2 | 6.0 | |
| Arousal | 3, 4, 5, 6 | 0 – 5 | 0.3 | 0 | 6.0 | |
| Lubrication | 7, 8, 9, 10 | 0 – 5 | 0.3 | 0 | 6.0 | |
| Orgasm | 11, 12, 13 | 0 – 5 | 0.4 | 0 | 6.0 | |
| Satisfaction | 14, 15, 16 | 0 (or 1) – 5 | 0.4 | 0.8 | 6.0 | |
| Pain | 17, 18, 19 | 0 – 5 | 0.4 | 0 | 6.0 | |
| | | Full Scale Score Range | | 2.0 | 36.0 | |

FIG. 9

| Average Scaled Score for 24 Respondents | | | Timing | | |
|---|---|---|---|---|---|
| Domain | Type | Question | Before Libby | After Libby | % Change |
| Arousal | frequency | Score: how often did you feel sexually aroused ("turned on") during sexual activity or intercourse? | 1.0 | 1.3 | 27% |
| Arousal | frequency | Score: how often have you been satisfied with your arousal (excitement) during sexual activity or intercourse? | 1.0 | 1.3 | 20% |
| Arousal | rating | Score: how confident were you about becoming sexually aroused during sexual activity or intercourse? | 0.9 | 1.2 | 31% |
| Arousal | rating | Score: how would you rate your level of sexual arousal ("turn on") during sexual activity or intercourse? | 1.0 | 1.2 | 25% |
| Desire | frequency | Score: how often did you feel sexual desire or interest? | 1.6 | 2.1 | 32% |
| Desire | rating | Score: how would you rate your level (degree) of sexual desire or interest? | 1.5 | 2.1 | 43% |
| Lubrication | frequency | Score: how often did you become lubricated ("wet") during sexual activity or intercourse? | 1.1 | 1.3 | 20% |
| Lubrication | frequency | Score: how often did you maintain your lubrication ("wetness") until completion of sexual activity or intercourse? | 1.1 | 1.3 | 18% |
| Lubrication | rating | Score: how difficult was it to become lubricated ("wet") during sexual activity or intercourse? | 1.2 | 1.3 | 7% |
| Lubrication | rating | Score: how difficult was it to maintain your lubrication ("wet") until completion of sexual activity or intercourse? | 1.2 | 1.2 | 8% |
| Orgasm | frequency | Score: when you had sexual stimulation or intercourse, how often did you reach orgasm (climax)? | 1.4 | 1.6 | 11% |
| Orgasm | rating | Score: how satisfied were you with your ability to reach orgasm (climax) during sexual activity or intercourse? | 1.2 | 1.6 | 30% |
| Orgasm | rating | Score: when you had sexual stimulation or intercourse, how difficult was it for you to reach orgasm (climax)? | 1.5 | 1.6 | 5% |
| Pain | frequency | Score: how often did you experience discomfort or pain during vaginal penetration? | 1.6 | 1.8 | 11% |
| Pain | frequency | Score: how often did you experience discomfort or pain following vaginal penetration? | 1.6 | 1.7 | 8% |
| Pain | rating | Score: how would you rate your level (degree) of discomfort or pain during or following vaginal penetration? | 1.6 | 1.8 | 7% |
| Satisfaction | rating | Score: how satisfied have you been with the amount of emotional closeness during sexual activity between you and your partner? | 1.4 | 1.6 | 13% |
| Satisfaction | rating | Score: how satisfied have you been with your overall sexual life? | 1.2 | 1.6 | 32% |
| Satisfaction | rating | Score: how satisfied have you been with your sexual relationship with your partner? | 1.2 | 1.7 | 34% |

FIG. 13

COMPOSITION FOR INCREASING SEXUAL DESIRE OR PLEASURE

CLAIM OF BENEFIT TO PRIOR APPLICATIONS

This application claims the benefit of and priority to U.S. Provisional Application No. 63/006,965 entitled "WOMEN'S SUPPLEMENT", filed on Apr. 8, 2020, the entire disclosure of which is hereby incorporated herein by reference in its entirety.

FIELD OF THE INVENTION

The field of the invention relates generally to compositions and associated methods for increasing sexual desire and/or alleviating symptoms of diminished sexual desire as preferably either self-identified or as indicated by the use of the standard questionnaire for evaluation of sexual desire (Female Sexual Function Index [FSFI]) by, among other things, increasing or normalizing sexual desire in a living subject, most especially in female mammals.

BACKGROUND

The following description includes information that may be useful in understanding the methods and compositions of the present disclosure. It is not an admission that any of the information provided herein is prior art or relevant to the present disclosure or that any publication specifically or implicitly referenced is prior art.

It is generally accepted that women's sexual desires naturally fluctuate over their lifetime. In addition to natural fluctuation, commonly prescribed medications used for mood disorders (e.g., selective serotonin reuptake inhibitors (SSRIs)) are known to lower the sex drive of women. Furthermore, some women have been known to also experience a decreased libido and sexual desire when taking birth control pills. Being evaluated for and obtaining a prescribed medication to alleviate a decreased libido caused naturally and/or from other prescribed medications is burdensome, possibly embarrassing, and may result in additional complications and/or side effects from additionally prescribed medications.

Regardless of the cause, many women suffer from a decreased sexual desire and many of those women would choose to remedy their decreased sex drive or simply increase their sexual desire if an over the counter and natural solution was readily available. The inventions described and claimed herein, increase sexual desire and/or pleasure in a female and provide various additional benefits and advantages described herein.

SUMMARY OF THE INVENTION

The current disclosure provides compositions and associated methods in the form of an oral dosage unit or supplement for increasing sexual desire and/or pleasure in a subject (female or male mammal). In at least one embodiment, the composition includes an effective combination of (1) damiana (*Turnera diffusa*), (2) ginseng, (3) saffron, (4) theacrine, (5) potassium nitrate, (6) vitamin B12, (7) and (8) vitamin C taken as an oral dosage unit, pill or capsule. In at least one other embodiment, the composition additionally includes one or more ingredients selected from (1) l-ergothioneine, (2) stabilized rice bran, and/or (3) sterilized rice hulls.

In yet another embodiment, a composition for increasing sexual desire or pleasure in a female is provided. The composition comprises (a) damiana (*Turnera diffusa*), (b) theacrine; (c) vitamin B12; (d) potassium nitrate; (e) saffron; and (f) vitamin C and is provided as an oral dosage unit, capsule or tablet.

In yet another embodiment, the composition further includes L-ergothioneine.

In yet another embodiment, the amount of L-ergothioneine in the composition is between 0.10 mg to 50 mg.

In yet another embodiment, the damiana provided is an extract and the extract is made from any aerial part of the damiana (*Turnera diffusa*) shrub.

In yet another embodiment, the amount of theacrine in the composition is between 5 mg to 800 mg, the amount of damiana (*Turnera diffusa*) in the composition is between 100 mg to 300 mg, the amount of vitamin B12 in the composition is between 2.4 micrograms to 1 mg, the amount of potassium nitrate in the composition is between 10 mg to 500 mg, the amount of saffron in the composition is between 5 mg to 500 mg and the amount vitamin C in the composition is between 10 mg to 500 mg.

In yet another embodiment, the composition further includes *Panax ginseng* or *Panax notoginseng*.

In yet another embodiment, a composition for increasing sexual desire or pleasure in a female is provided. The composition comprises (a) damiana (*Turnera diffusa*), (b) theacrine, (c) vitamin B12, (d) potassium nitrate, (e) saffron, (f) vitamin C and (g) L-ergothioneine and the composition is provided as an oral dosage unit, capsule or tablet.

In yet another embodiment, a method of increasing sexual desire in a mammal is provided. The method comprises administering or providing to a mammal in need thereof a composition comprising (a) damiana (*Turnera diffusa*), (b) theacrine, (c) vitamin B12, (d) potassium nitrate, (e) saffron and (f) vitamin C and the composition is administered or provided to the mammal as an oral dosage unit, capsule or tablet.

In yet another embodiment, the total weight of the active ingredients in a single dose of the composition is not more than 1,500 mg.

In yet another embodiment, the damiana (*Turnera diffusa*) in the composition is an extract of damiana made from any aerial part of the damiana shrub. In yet another embodiment, the composition includes damiana extract at or between about 0.1 mg to 1.0 gram per oral dosage unit.

In yet another embodiment, the composition includes theacrine at or between about 5 to 800 mg per oral dosage unit.

In yet another embodiment, the composition includes vitamin B12 at or between about 2.4 micrograms to 1 mg per oral dosage unit.

In yet another embodiment, the composition includes potassium nitrate at or between about 10 to 500 mg per oral dosage unit.

In yet another embodiment, the composition includes *ginseng* at or between about 50 to 800 mg per oral dosage unit.

In yet another embodiment, the composition includes saffron at or between about 5 mg to 500 mg per oral dosage unit.

In yet another embodiment, the composition includes vitamin C at or between about 10 mg to 500 mg per oral dosage unit.

In yet another embodiment, in addition to damiana, saffron, *ginseng*, theacrine, vitamin B12, potassium nitrate, and vitamin C, the composition also includes L-ergothioneine.

In yet another embodiment, the *ginseng* is in the form of dried root powder or an extract.

In yet another embodiment, the *ginseng* is a *Panax ginseng* extract or a *Panax Notoginseng* extract.

In yet another embodiment, the composition also includes L-ergothioneine at or between 0.1 mg to 50 mg per oral dosage unit.

In yet another embodiment, the composition for increasing or normalizing sexual desire or pleasure in a subject includes damiana (*Turnera diffusa*) extract, theacrine, vitamin B12, potassium nitrate, vitamin C, saffron, *ginseng*, and L-ergothioneine, where the components of the composition make up at least 50% by weight of the total weight of the composition. In yet another embodiment, the components of the composition make up at least 80% by weight of the total weight of the composition. In yet another embodiment, the composition also includes an emulsifying agent and/or an anti-caking agent. In yet another embodiment, the emulsifying agent is a rice extract (e.g., stabilized rice bran) and the anti-caking agent is rice hulls.

In yet another embodiment, methods of increasing sexual desire in a mammal and/or increasing a mammal's ability to achieve an orgasm is provided. The methods include providing or administering the compositions disclosed herein to a mammal in need thereof. In at least one aspect of at least one embodiment, the mammal is a female mammal. In at least one aspect of at least one embodiment, the mammal is a female human.

In yet another embodiment, methods of reducing vaginal dryness and/or enhancing clitoral sensation in a mammal is provided. The methods including providing or administering the compositions disclosed herein to a mammal in need thereof.

In yet another embodiment, the composition ingredients are all natural compounds, and the compositions do not include any synthetic or artificial components. For example, in at least one embodiment, the compositions are a natural supplement and is not a pharmaceutical medicament (e.g., drug).

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIGS. 1-5 shows Female Sexual Function Index (FSFI) questionnaire.

FIGS. 6-8 shows FSFI Scoring Appendix.

FIG. 9 shows FSFI DOMAIN SCORES AND FULL SCALE SCORE which shows how the questionnaires completed by the humans who took the claimed composition were scored. The individual domain scores and full scale (overall) score of the FSFI can be derived from the computational formula outlined in the table shown. For individual domain scores, add the scores of the individual items that comprise the domain and multiply the sum by the domain factor. Add the six domain scores to obtain the full scale score. It should be noted that within the individual domains, a domain score of zero indicates that the subject reported having no sexual activity during the past month. Subject scores can be entered in the right-hand column.

FIG. 13 shows a table representation of average scaled scores for various indicated questions for the 24 humans that took the claimed composition (referred to in the table as "Libby") both before and after taking the claimed composition.

DETAILED DESCRIPTION

Figure 10:
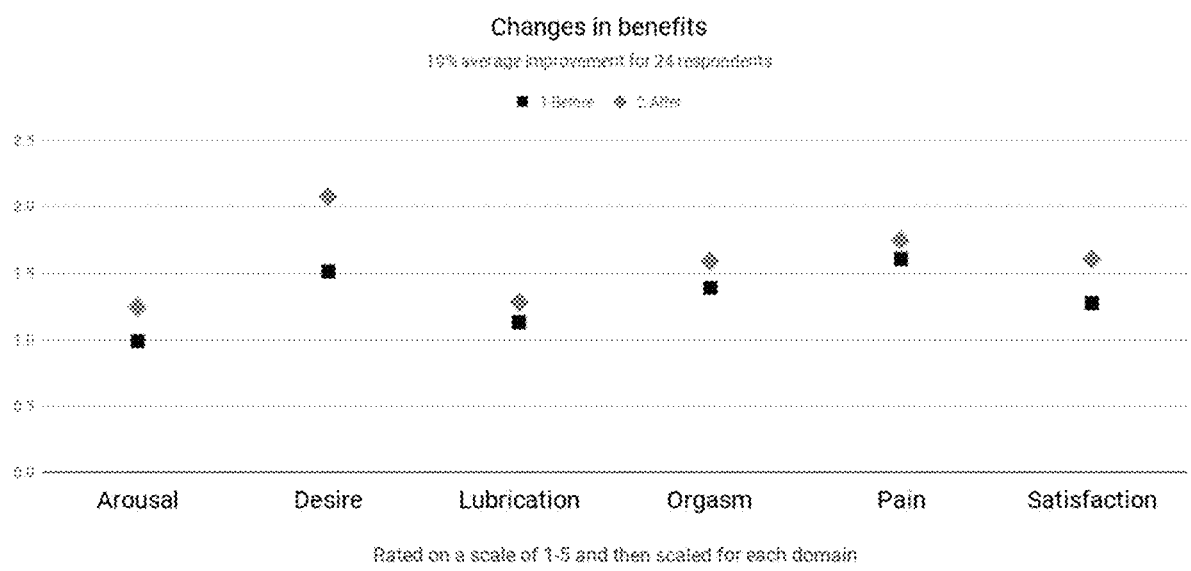
FIG. 10 shows a graph of the results of the detailed questionnaire given to humans that took the compositions claimed in the present disclosure and the average score showing changes in benefits for arousal, lubrication, design, orgasm, pain and satisfaction separately. The results show both before and after the claimed compositions was taken by female respondents.

The methods and compositions disclosed herein provide, among other things, effective methods and compositions to alleviate diminished sexual desire or increase sexual desire in a mammal. The effectiveness of the presently disclosed supplement may be evident in both men and women.

Any increase in sexual desire, whether an increase from a diminished level or an increase from what may be a normalized level for the subject, may be either self-determined or measured utilizing the Female Sexual Function Index (FSFI) questionnaire.

As used herein "subject," "mammal," or "mammal subject" may be used interchangeably to refer to any mammal to which the presently disclosed compositions may be applied or administered. The mammal does not need to be suffering from any health-related condition or disease to benefit from the presently disclosed compositions and methods. The subject may simply choose or be desirous of stimulating or increasing sexual desire. As such, any subject may consume the disclosed compositions or be a recipient of the disclosed methods. While the subject or mammal may include female and male subjects, including both humans and animals (e.g., domesticated animals), the contemplated composition is particularly effective for female mammals.

As used herein, "administering" and like terms refer to the step of providing to and includes self-administering. Administering of any of the presently disclosed compositions include any mode by which the mammal (e.g. a male or female subject) can ingest the composition. Any suitable means of administration may be used so long as the composition is ingested and reaches the bloodstream. For example, a composition may be orally ingested by any mode encompassed by the Dietary Supplement Health and Education Act of 1994 (DSHEA).

Effective Blend of Active Ingredients

The compositions and associated methods disclosed herein increase sexual desire (e.g., libido) or alleviate symptoms and causes of diminished sexual desire. In one embodiment, the composition includes at least damiana (*Turnera diffusa*), theacrine, *ginseng*, saffron, potassium nitrate, vitamin C and vitamin B12. In another embodiment, the composition includes damiana (*Turnera diffusa*), theacrine, *ginseng*, saffron, potassium nitrate, vitamin C, vitamin B12 and L-ergothioneine. It should be appreciated that the compositions disclosed and claimed herein can be provided with other additives, fillers, and/or excipients or with the ingredients alone. In yet another embodiment, the ingredients of the composition make up at least 50% by weight of the total weight of all ingredients in the composition. Additionally, in yet other embodiments, the effective blend of the ingredients of the composition makes up at least 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.9%, or 100% by weight of the total weight of all ingredients in the composition.

In yet another embodiment, the composition is a blend of damiana (*Turnera diffusa*), theacrine, *ginseng*, saffron, potassium nitrate, vitamin C, and vitamin B12 which in combination confer a synergistic effectiveness not found in a formulation lacking one or more of these ingredients. The combination of damiana (*Turnera diffusa*), theacrine, saffron, *ginseng*, potassium nitrate, vitamin C, and vitamin B12 act synergistically together to confer additional benefits. This is also true of the addition of L-ergothioneine. Advantageously, in combination, this effective blend of ingredients confers an increase in sexual desire. As used herein, sexual desire and libido are used interchangeably.

In yet another embodiment, a blend of damiana, theacrine, *ginseng*, saffron, potassium nitrate, vitamin C, and vitamin B12 and L-ergothioneine is provided.

The effectiveness in increasing sexual desire or alleviating diminished sexual desire in a subject by administering the presently disclosed composition may be determined from testimonials and questioners of volunteers. The reported effects from the presently contemplated blend include an increase in sexual desire, reduction of vaginal dryness, a greater frequency of sexual intercourse and orgasm, and/or enhanced clitoral sensation. Additionally, or alternatively, effects from the presently contemplated blend may include an improved score on the standard FSFI questionnaire used to evaluate sexual satisfaction.

In yet another embodiment, about 100 mg (0.1 gram) up to about 1000 mg (1.0 gram) damiana (*Turnera diffusa*) extract is provided to the mammal as an oral dosage to take daily. In an aspect of at least one embodiment of in this disclosure, a single dose of the composition disclosed herein includes at or between about 100, 15 mg, 200 mg, 250 mg, 300 mg, 350 mg, 400 mg, 425 mg, 450 mg, 475 mg, 500 mg, 525 mg, 550 mg, 575 mg, 600 mg, 650 mg, 700 mg, 750 mg, 800 mg, 850 mg, 900 mg, or 950 mg of a damiana extract. In at least one embodiment of the present disclosure, a single dose of the composition includes damiana extract at or between about 100 to 300 mg. In one aspect of at least one embodiment, the damiana extract may be made from any aerial part of the damiana (*Turnera diffusa*) shrub. The contemplated composition combines damiana in an effective blend of other active ingredients to improve and address other mood, circulation, and/or energy aspects that may interfere with a subject's libido.

In yet another embodiment, about 5 mg up to 500 mg saffron is provided to a mammal as a single dose. In an aspect of at least one embodiment of in this disclosure, a single dose of the composition disclosed herein includes at or between about 5 mg, 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, or 500 mg saffron. In at least one embodiment of the present disclosure, a single dose of the composition includes saffron at or between about 5 mg up to about 100 mg. In yet aspect of at least one embodiment, a single dose of the composition includes saffron at or between about 10 mg up to about 40 mg. Saffron. The embodiments disclosed herein combines saffron in an effective blend of other ingredients to improve and address other mood or energy aspects to effectively enhance a subject's libido.

In yet another embodiment, at or between about 2.4 ug up to 1 mg vitamin B12 is provided as a single dose of the composition. In another embodiment, a single dose of the composition includes vitamin B12 at or between about 0.020 mg up to 0.2 mg (200 ug). In yet another embodiment, a single dose of the composition includes vitamin B12 at or between 0.040 mg to 0.060 mg. The compositions disclosed herein combine vitamin B12 which acts synergistically with the other ingredients to effectively enhance a subject's libido.

In yet another embodiment, a single dose of the composition includes at or between about 10 mg up to about 500 mg potassium nitrate. In yet another embodiment, a single dose of the composition includes potassium nitrate at or between about 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, or 500 mg. In another aspect of at least one embodiment, a single dose of the composition includes potassium nitrate at or between about 100 to 400 mg. Potassium nitrate (KNO3) is known to enhance nitric oxide which increases blood flow in the body. The compositions disclosed combines KNO3 with the other ingredients that work synergistically to improve and increase and enhance the recipient's libido.

In yet another embodiment, a single dose of the composition includes at or between about 10 mg up to about 500 mg vitamin C. In yet another embodiment, a single dose of the composition includes vitamin C at or between about 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 450 mg, or 500 mg. In yet another embodiment, a single dose of the composition includes vitamin C at or between about 10 mg to 300 mg. In yet another embodiment, a single dose of the composition includes vitamin C at or between about 50 mg to 250 mg. A non-limiting exemplary form of vitamin C includes ascorbic acid. The compositions disclosed herein combines vitamin C with the ingredients of the composition which work synergistically to improve and address blood flow to effectively enhance a subject's libido.

With respect to the theacrine component, a single dose of the composition may include at or between about 5 mg up to about 800 mg. Typically, a single dose of the composition includes at or between about 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 325, 350, 375, 400, 425, 450, 475, 500, 525, 550, 575, 600, 650, 700, 750, or 800 mg of theacrine. More typically, a single dose of the composition includes theacrine at or between about 20 to 80 mg. Theacrine is known to increase energy in a subject (e.g., mammal, human). The contemplated composition combines theacrine an effective blend of other active ingredients to improve and address the energy level and mood in a subject to effectively enhance the subject's libido.

With respect to the *ginseng* component, the composition may include dried *ginseng* root powder or an extract of *ginseng*. Types of *ginseng* include *Panax ginseng* (e.g., Asian, Korean, or Chinese *ginseng*.) Preferably, the composition includes a *ginseng* extract. Extracts may be from any *Panax ginseng*, and may also be further processed or concentrated. Preferably, the *ginseng* is a *Panax ginseng* extract, and more preferably the *ginseng* is *Panax notoginseng* extract. In some embodiments, a single dose of the composition may include at or between about 50 mg up to about 800 mg *ginseng*. For example, a single form of the composition includes *ginseng* (e.g., root powder or extract) at or between about 50, 60, 70, 80, 90, 100, 125, 150, 175, 200, 225, 250, 275, 300, 325, 350, 375, 400, 450, 500, 525, 550, 575, 600, 650, 700, 750, or 800 mg. Typically, a single dose of the composition includes *ginseng* at or between about 50 to 500 mg. More typically, a single composition includes *ginseng* at or between about 100 to 300 mg. *Ginseng* and in particular *Panax ginseng* has been reported to lower blood pressure in mammals. See, e.g., Kim, 2018, *J. Ginseng Res.*, 42:264-269. The contemplated composition combines *ginseng* in an effective blend of other active ingredients to effectively enhance a subject's libido.

With respect to an L-ergothioneine component, a single dose of the composition may include at or between about 0.1 mg up to about 50 mg L-ergothioneine. For example, a single dose of the composition includes L-ergothioneine at or between about 0.1, 0.20, 0.25, 0.030, 0.35, 0.40, 0.45, 0.50, 0.60, 0.65, 0.70, 0.80, 0.90, 1, 5, 10, 15, 20, 25, 30, 35, 40, 45, or 50 mg. Typically, a single dose of the composition includes L-ergothioneine at or between about 0.10 to 0.70 mg. More typically, a single dose of the composition includes L-ergothioneine at or between about 0.20 to 0.60 mg. L-ergothioneine is an antioxidant known to support and enhance the effects of vitamin C. The contemplated composition combines L-ergothioneine in an effective blend of other active ingredients to effectively enhance a subject's libido.

While contemplated compositions of an effective blend of the active ingredients as disclosed herein may be formulated in numerous manners, it is generally preferred that the composition is formulated as a tablet, a capsule, a ready-to-mix formulation or other compatible solid or oral liquid dosage form commonly used to deliver dietary supplement ingredients. Most preferably, contemplated compositions are in tablet or capsule form formulated to provide no more than 1,500 mg of all active ingredients (damiana, theacrine, vitamin C, vitamin B12, potassium nitrate, saffron, *ginseng*, (and optionally L-ergothioneine) in a recommended daily dose.

In still further contemplated uses of any botanical active ingredient including damiana and *ginseng*, it is contemplated that the effective amount of the botanical includes the root, extract, derivative, or analog thereof. Furthermore, the root (*ginseng* or damiana) may be employed as starting material for extraction of various beneficial components. For example, the damiana root and/or the *ginseng* root may be used in root form, more preferably, the damiana and *ginseng* root are extracted. For example, the damiana and/or *ginseng* may be extracted with an aqueous (e.g., water, water-ethanol mixture) or non-aqueous solvent (e.g., critical point $CO_2$, dimethylformamide) to isolate one or more components that can be used in the composition product.

With reference to Table 1, the active ingredients are shown including the weight ranges of each active ingredient component and weight.

TABLE 1

Ingredients for Composition (e.g., tablet or capsule)

| Active Ingredient | Weight amount per single composition form | Exemplary Amount in one capsule dose (2 capsules taken daily) | Exemplary Brand Name (Manufacturer) |
|---|---|---|---|
| Damiana (*Turnera diffusa*) | 100 to 1000 mg | 150 mg | Liboost ® (PharmActive) |
| Theacrine | 5 to 800 mg | 25 mg | Teacrine ® (Compound Solutions) |
| Saffron | 5 to 500 mg | 14 mg | Affron ® (PharmActive) |
| Potassium Nitrate | 10 to 500 mg | 150 mg | |
| Vitamin B12 | 2.4 ug to 1 mg | 0.05 mg | |
| Ginseng | 50 to 800 mg | 100 mg | NotoGinseng ™/Ginseng Plus ® (Farlong ®) |
| Vitamin C | 10 to 500 mg | 100 mg | |
| L-ergothioneine | 0.10 to 50 mg | 0.25 mg | Ergoneine ® (Tetrahedon) |

The composition having the disclosed effective blend of active ingredients is formed in an orally administrable supplement. In addition to the active ingredients, the composition may also include additional components such as excipients, additives, binders, and thickening agents useful for the preparation of desired formulations (e.g., tablet, capsule, or a ready-to-mix formulation). Non-limiting examples include non-toxic compatible fillers, binders such as starch, polyvinyl pyrrolidone or cellulose ethers, disintegrants such as sodium starch glycolate, crosslinked polyvinyl pyrrolidone or croscarmellose sodium, buffers, preservatives, anti-oxidants, lubricants, flavorings, thickeners, coloring agents, wetting agents such as sodium lauryl sulfate, emulsifiers and the like. The amount of excipient or additive can range from about 0.1 to about 50 percent of the total weight of the composition with the active ingredients making up at least 50% of the total weight. One skilled in the art would understand that the amount of carrier(s), excipients and additives (if present) can vary.

It is generally preferred that the contemplated composition according to the inventive subject matter will be orally administered, and all known forms of oral administration are deemed suitable for use herein, including solid and liquid forms. For example, solid oral forms include capsules, tablets, lozenges, powders, while preferred liquid oral forms include solutions or suspensions in suitable medium (typically aqueous solution). The oral form of the disclosed composition includes any composition that can be ingested pursuant with the Dietary Supplement Health and Education Act of 1994 (DSHEA). Accordingly, the inventive subject matter includes a dietary supplement made with the composition as disclosed herein having at least the effective blend of the disclosed active ingredients.

Acceptable carriers and excipients to be combined with the active ingredients include fillers or extenders, binders, wetting agents, emulsifiers, and anti-caking agents. Preferably additional non-active ingredient components which aid in the formation and stability of the composition are natural products, and more preferably they are organic natural products. Typically, additional non-active ingredient components are considered "clean label" components. The term "clean label" is a widely used term that refers to making a product with as few ingredients as possible using wholesome, natural ingredients that may also contribute nutritional value by virtue of their composition. More typically, all of the active and non-active ingredients are natural, rendering the composition a natural product alternative to most pharmaceutical compositions. Advantageously, use of the composition allows for treatment of a diminished libido and related methods thereof, using a composition that is void of synthetic or artificial components, and is not a pharmaceutical medicament (e.g., a drug).

Exemplary non-active ingredient components to aid in the formation and stability of the composition include a natural emulsifier and a natural anti-caking agent. In some embodiments, a natural emulsifier includes rice extract, also referred to as rice bran extract. Typically, the contemplated composition includes 40 to 120 mg rice extract in each single form of the composition. More typically, the contemplated composition includes 60 to 80 mg rice extract in each single form of the composition. Nu-RICE® manufactured by Ribus® is a preferred example of a stabilized rice bran extract. In some embodiments, a natural anti-caking agent includes sterilized and ground rice hulls. Typically, the contemplated composition includes 20 to 80 mg rice hulls in each single form of the composition. More typically, the contemplated composition includes 30 to 50 mg rice hulls in each single form of the composition. Nu-FLOW® made by Ribus® is a preferred example of sterilized, ground rice hulls.

While natural carriers and excipients are preferred, the contemplated composition may be made with any suitable carrier or excipient regardless of whether or not the components are natural, and so long as the composition includes at least the effective blend of active ingredients as disclosed herein. Exemplary suitable acceptable carriers include fillers or extenders (e.g., starch, lactose, sucrose, glucose, mannitol, and/or silicic acid), binders (e.g., alginates, gelatin, carboxymethylcellulose, or polyvinyl pyrolidone), humectants (e.g., glycerol), disintegrating agents (e.g., agar-agar, calcium carbonate, or potato or tapioca starch), solution retarding agents (e.g., paraffin), absorption accelerators (e.g., quaternary ammonium salts), wetting agents (e.g., cetyl alcohol, glycerol monostearate), absorbents (e.g., kaolin, bentonite clay), lubricants (e.g. talc, calcium stearate, magnesium stearate, solid polyethylene glycols), coloring agents, buffers, etc.

Contemplated oral solid dosage may also be formulated to provide slow or controlled release of the active ingredient (e.g., using hydroxypropylmethyl cellulose in varying proportions to provide a desired release profile, other polymer matrices, liposomes and/or microspheres). It should be appreciated that preparation of contemplated oral solid dosage forms is well known in the art, and all of the known methods are deemed suitable for use in conjunction with the teachings presented herein.

Liquid dosage forms for oral administration of contemplated compounds may be prepared as acceptable emulsions, micro-emulsions, solutions, suspensions, syrups and elixirs. Therefore, and depending on the particular formulation, the liquid dosage forms may also contain inert diluents, including water or other aqueous and non-aqueous solvents, solubilizing agents and emulsifiers (e.g., ethyl alcohol, isopropyl alcohol, ethyl carbonate, ethyl acetate, benzyl alcohol, etc.), suspending agents (e.g., ethoxylated isostearyl alcohols, polyoxyethylene sorbitol), oils (e.g., cottonseed, corn, germ, olive, etc.), glycerol, tetrahydrofuryl alcohol, polyethylene glycols, and further known acceptable liquid components.

Treatment of Diminished Sexual Desire

The inventive subject matter includes methods for alleviating diminished sexual desire in a subject. In particular, increasing sexual desire and/or alleviating diminished sexual desire in a subject includes increasing the subject's ability to have an orgasm, reducing vaginal dryness in a female subject, and/or enhancing clitoral sensation in a female subject. These methods include administering (e.g., orally) the disclosed composition having an effective blend of the active ingredients to the subject. Whereas the subject may be a female or male mammal, the subject is typically a female mammal. More typically, the subject is a female human.

The contemplated subject matter also includes methods for alleviating diminished sexual desire in a subject caused by prescription pharmaceutical medications used for mood disorders (e.g., selective serotonin reuptake inhibitors (SSRIs)) as well as birth control medications. Birth control medications known to decrease sexual desire are hormone medicaments including at least one of estrogen and progestin or derivatives of either thereof. Methods for alleviating these sexual side effects include administration to the subject of the composition having an effective blend of active ingredients as disclosed herein. The composition may be taken sporadically or daily. For example, the composition may be taken concurrently with the prescribed medication.

Additionally, methods for decreasing anxiety and/or treating a mood disorder in a subject irrespective of prescribed medications include administration to the subject of the composition having an effective blend of active ingredients as disclosed herein. The composition may be taken sporadically or daily.

In more specific embodiments, the composition may be taken orally by a subject (person or mammal) to increase sexual desire for an acute period of time or over a long period of time. For example, the composition may be taken 1 to 2 times a day on a daily basis for any period of time. The composition may be taken orally 1 to 2 times a day for a month, a week, or 1 to 3 days. Furthermore, a preferred effective dosage of the composition may include two of the supplement forms. For example, a single form includes the weight amounts provided herein (e.g., Table 1), however an effective dosage may include two capsules, tablets, or any suitable solid or liquid form as disclosed herein. Accordingly, an effective dosage of the composition may be at least two solid or liquid forms taken orally by the subject for an acute period of time or over a long period of time as disclosed. Depending on results, the subject may increase the dosage to more than two.

Effectiveness of the contemplated composition may be assessed by any suitable protocol. For example, the assessment may be self-determined by the subject taking the composition. A subject's observation or testimonial of increased sexual desire is an exemplary means of measuring effectiveness of the composition. Effectiveness of the composition may vary from subject to subject.

In addition, determination of effectiveness of the composition may be carried out using the Female Sexual Function Index (FSFI) Questionnaire (FIGS. 1-5). The FSFI questionnaire may be considered by the subject or another to determine effectiveness. Preferably, the FSFI questionnaire is completed before administration of the composition and again after at least one period of administration of the supplement composition. If the answers on the questionnaire change along the lines of increased sexual desire in the questionnaire taken after administration, the composition is considered effective. Preferably, the FSFI Questionnaire is scored following the FSFI Scoring Appendix (FIGS. 6-9). If the subject's FSFI Questionnaire score for the questionnaire taken after administration increases compared to the score on the questionnaire taken prior to administration, the composition is considered effective. Each of the 19 questions on questionnaire fall into 1 of 6 "domains" (desire, arousal, lubrication, orgasm, satisfaction, and pain) with a rating of 1-5. (The pain rating is recorded as an improvement, so a 5 means least pain). Each question is either about frequency ("how often") or intensity ("satisfaction", "confidence", "lack of pain" etc). In cases where a female respondent missed either the 2-week survey or the 4-week survey their last submitted survey was used. The ratings are scaled by the factor listed FIG. 9 to get a scaled score.

Figure 11:
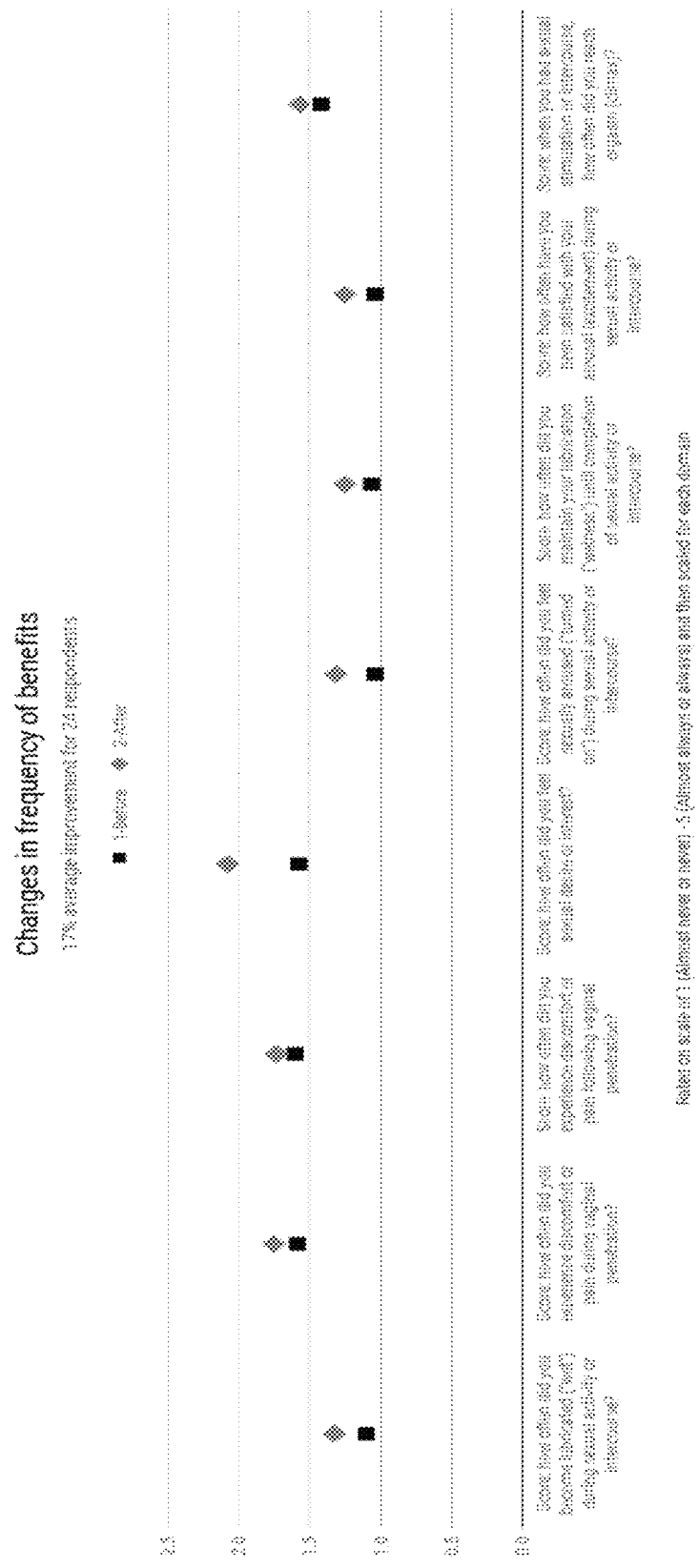
FIG. 11 shows a graph of the results of the detailed questionnaire given to humans that took the composition claimed in the present disclosure and the average score that was tabulated from the completed questionnaires for all the frequency related questions answered by the humans both before taking the composition claimed in the present disclosure vs after taking the compositions claimed in the present disclosure.
Figure 12:
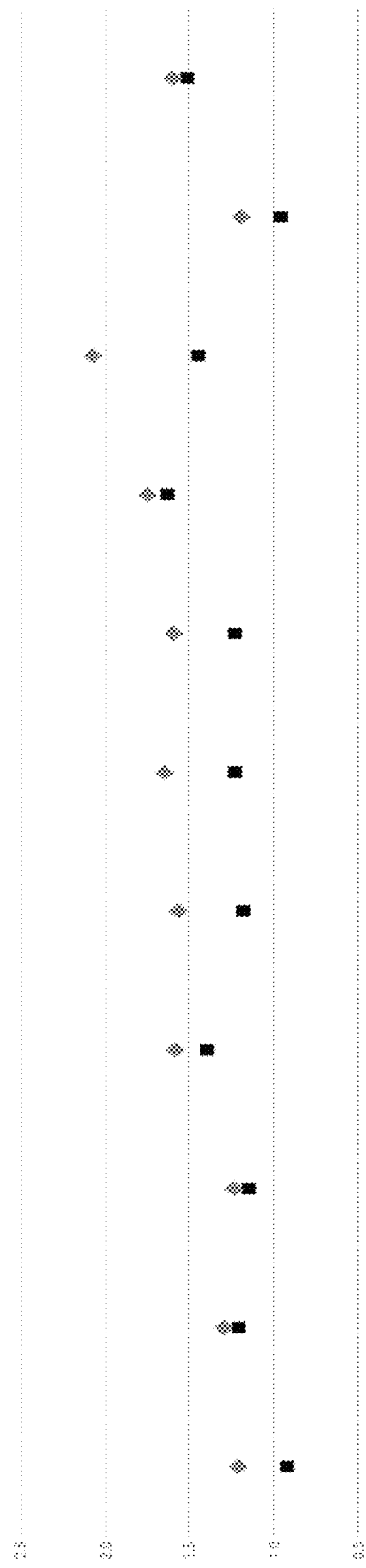
FIG. 12 shows a graph of the results of the detailed questionnaire given to humans that took the composition claimed in the present disclosure and the average score that was tabulated from the completed questionnaires for all the intensity related questions answered by the humans both before taking the claimed composition in the present disclosure vs after taking the composition claimed in the present disclosure.

The data shown in FIGS. 10-13 represents the responses of 24 female respondents. Each completed a (FSFI) Questionnaire prior to starting consumption of 2 capsules of the composition claimed herein, which in one embodiment contains (a) damiana (*Turnera diffusa*). (b) theacrine; (c) vitamin B12; (d) potassium nitrate; (e) saffron; (f) vitamin C, (g) ginseng and (h) L-ergothioneine per day. The of the female respondents submitted a final FSFI Questionnaire at 2 or 4 weeks after taking the composition indicated above. There was a 19% average improvement measured in the FSFI responses completed by the female respondents. Every question demonstrated improvement across each of the domains of desire, arousal, lubrication, orgasm, satisfaction, and pain as shown and demonstrated in FIGS. 10-13. The data shown in the attached FIGS. demonstrates that the ingredients of the claimed compositions work together synergistically to provide the unexpected indicated benefits to the female respondents that is more than the additive sum of the benefits one could expect to receive from the various ingredients separately.

The discussion presented herein provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported statistically significant measurements and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates to the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A composition for increasing sexual desire and pleasure in a female, the composition comprising:
   (a) damiana (*Turnera diffusa*);
   (b) theacrine;
   (c) vitamin B12;
   (d) potassium nitrate;
   (e) saffron; and
   (f) vitamin C;
   wherein the composition is provided as an oral dosage unit which is in the form of a, capsule or tablet.

2. The composition of claim 1, wherein the composition further includes L-ergothioneine.

3. The composition of claim 2, wherein the amount of L-ergothioneine in the composition is between 0.10 mg to 50 mg.

4. The composition of claim 1, wherein the damiana provided is an extract.

5. The composition of claim 4, wherein the extract is made from any aerial part of the damiana (*Turnera diffusa*) shrub.

6. The composition of claim 1, wherein the amount of theacrine in the composition is between 5 mg to 800 mg.

7. The composition of claim 6, wherein the amount of damiana (*Turnera diffusa*) in the composition is between 100 mg to 300 mg, the amount of vitamin B12 in the composition is between 2.4 micrograms to 1 mg, the amount of potassium nitrate in the composition is between 10 mg to 500 mg, the amount of saffron in the composition is between 5 mg to 500 mg and the amount vitamin C in the composition is between 10 mg to 500 mg.

8. The composition claim 1, wherein composition further includes *Panax ginseng* or *Panax notoginseng*.

9. A composition for increasing sexual desire and pleasure in a female, the composition comprising:
   (a) damiana (*Turnera diffusa*);
   (b) theacrine;
   (c) vitamin B12;
   (d) potassium nitrate;
   (e) saffron;
   (f) vitamin C; and
   (g) L-ergothioneine;
   wherein the composition is provided as an oral dosage unit which is in the form of a, capsule or tablet.

10. The composition of claim 9, wherein the damiana provided is an extract.

11. The composition of claim 10, wherein the extract is made from any aerial part of the damiana (*Turnera diffusa*) shrub.

12. The composition of claim 9, wherein the amount of theacrine in the composition is between 5 mg to 800 mg.

13. The composition of claim 12, wherein the amount of damiana (*Turnera diffusa*) in the composition is between 100 mg to 300 mg, the amount of vitamin B12 in the composition is between 2.4 micrograms to 1 mg, the amount of potassium nitrate in the composition is between 10 mg to 500 mg, the amount of saffron in the composition is between 5 mg to 500 mg, the amount vitamin C in the composition is between 10 mg to 500 mg and the amount of L-ergothioneine in the composition is between 0.20 to 0.60 mg.

* * * * *